US009611193B2

(12) United States Patent
Choi et al.

(10) Patent No.: US 9,611,193 B2
(45) Date of Patent: Apr. 4, 2017

(54) OLEFIN CONVERSION PROCESS

(71) Applicant: Lummus Technology Inc., Bloomfield, NJ (US)

(72) Inventors: Sukwon Choi, Clifton, NJ (US); Bala Ramachandran, Easton, PA (US)

(73) Assignee: Lummus Technology Inc., Bloomfield, NJ (US)

( * ) Notice: Subject to any disclaimer, the term of this patent is extended or adjusted under 35 U.S.C. 154(b) by 4 days.

(21) Appl. No.: 14/874,789

(22) Filed: Oct. 5, 2015

(65) Prior Publication Data

US 2016/0023964 A1     Jan. 28, 2016

Related U.S. Application Data

(62) Division of application No. 14/548,500, filed on Nov. 20, 2014, now Pat. No. 9,242,908.

(60) Provisional application No. 61/906,637, filed on Nov. 20, 2013.

(51) Int. Cl.
| | |
|---|---|
| *C07C 6/04* | (2006.01) |
| *C07C 5/27* | (2006.01) |
| *B01J 8/04* | (2006.01) |
| *C07C 5/25* | (2006.01) |
| *C07C 41/05* | (2006.01) |
| *C07C 7/04* | (2006.01) |
| *B01J 8/00* | (2006.01) |

(52) U.S. Cl.
CPC ................ *C07C 6/04* (2013.01); *B01J 8/001* (2013.01); *B01J 8/04* (2013.01); *C07C 5/2512* (2013.01); *C07C 5/277* (2013.01); *C07C 7/04* (2013.01); *C07C 41/05* (2013.01); *B01J 2208/027* (2013.01); *C07C 2521/04* (2013.01); *C07C 2521/06* (2013.01); *C07C 2521/08* (2013.01); *C07C 2521/10* (2013.01); *C07C 2523/02* (2013.01); *C07C 2523/30* (2013.01); *C07C 2529/06* (2013.01); *Y02P 20/127* (2015.11)

(58) Field of Classification Search
CPC ...... C07C 6/04; B01J 8/001; B01J 8/04; B01J 8/0453; B01J 8/0457
See application file for complete search history.

(56) References Cited

U.S. PATENT DOCUMENTS

2004/0267067 A1* 12/2004 Bridges ................ C07C 5/2568
                                                          585/324

* cited by examiner

*Primary Examiner* — Lessanework Seifu
(74) *Attorney, Agent, or Firm* — Osha Liang LLP

(57) ABSTRACT

A process for the production of $C_4$ olefins, which may include: contacting a hydrocarbon mixture comprising alpha-pentenes with an isomerization catalyst to form an isomerization product comprising beta-pentenes; contacting ethylene and the beta-pentenes with a first metathesis catalyst to form a first metathesis product comprising butenes and propylene, as well as any unreacted ethylene and $C_5$ olefins; and fractionating the first metathesis product to for an ethylene fraction, a propylene fraction, a butene fraction, and a $C_5$ fraction.

20 Claims, 3 Drawing Sheets

OLEFIN CONVERSION PROCESS

CROSS-REFERENCE TO RELATED APPLICATION

This application, pursuant to 35 U.S.C. §120, claims benefit to U.S. patent application Ser. No. 14/548,500 filed Nov. 20, 2014, now U.S. Pat. No. 9,242,908, which pursuant to 35 U.S.C. §119(e), claims priority to U.S. Provisional Application Ser. No. 61/906,637, filed Nov. 20, 2013. Each of these applications is incorporated herein by reference in their entirety.

BACKGROUND OF DISCLOSURE

Field of the Disclosure

Embodiments disclosed herein relate generally to the processing of a $C_5$ olefin stream, such as may be formed from a $C_5$ hydrocarbon cut from a cracking process, for conversion of the $C_5$ olefins to butenes via isomerization and metathesis.

Background

It is known to convert pentenes to propylene via metathesis. For example, when linear pentenes are fed to a conventional metathesis reactor, having a catalyst bed including a mixture of isomerization and metathesis catalysts, the following reactions may occur:

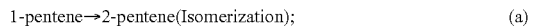

1-pentene→2-pentene(Isomerization);  (a)

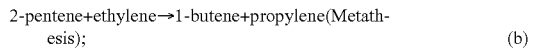

2-pentene+ethylene→1-butene+propylene(Metathesis);  (b)

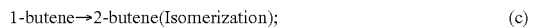

1-butene→2-butene(Isomerization);  (c)

2-butene+ethylene→2propylene(Metathesis).  (d)

1-Pentene is isomerized to 2-pentene. The metathesis reaction of 1-pentene with ethylene is non-productive (products are same as reactants). The overall linear $C_5$ olefin reaction for the production of propylene can thus be shown as:

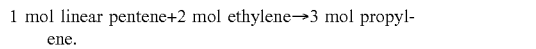

1 mol linear pentene+2 mol ethylene→3 mol propylene.

Butadiene demand, however, is increasing. Butadiene is a versatile raw material used in the production of a wide variety of synthetic rubbers, polymer resins and chemical intermediates. The largest uses for butadiene are the production of styrene butadiene rubber and polybutadiene rubber, which are used mainly in tire products. Butadiene is also one of the components used in the manufacture of acrylonitrile-butadiene-styrene, styrene-butadiene copolymer latex, styrene-butadiene block copolymers and nitrile rubbers. There is a growing demand for butadiene caused by the growth in tire demand as well as reduced natural rubber production.

The major source of butadiene is as a byproduct in the steam cracking of naphtha and gas oil to make ethylene and propylene. Steam cracking is a process by which hydrocarbon molecules are exposed to very hot steam, causing them to break apart into smaller molecules. Separation of butadiene from the other products of the steam cracking process typically includes the use of extractive distillation. Other potential sources for the production of butadiene include converting feed stocks comprising butene and butane compounds and mixtures thereof to butadiene.

SUMMARY OF THE DISCLOSURE

Embodiments disclosed herein relate generally to the production of butenes from a $C_5$ feedstock. The processes disclosed herein provide for converting a low-valued stream, $C_5$'s, for which demand is decreasing, such as due to regulatory changes decreasing RVP requirements and thus limiting $C_5$ blending in fuels, to a higher valued product, including butenes or butenes and propylene.

In one aspect, embodiments disclosed herein relate to a process for the production of $C_4$ olefins, the process comprising: contacting a hydrocarbon mixture comprising alpha-pentenes with an isomerization catalyst to form an isomerization product comprising beta-pentenes; contacting ethylene and the beta-pentenes with a first metathesis catalyst to form a first metathesis product comprising butenes and propylene, as well as any unreacted ethylene and $C_5$ olefins; and fractionating the first metathesis product to for an ethylene fraction, a propylene fraction, a butene fraction, and a $C_5$ fraction.

In another aspect, embodiments disclosed herein relate to a process for the production of $C_4$ olefins. The process may include: feeding ethylene and a $C_5$ olefin stream comprising a mixture of $C_5$ olefins including at least one of 1-pentenes, 2-methyl-1-butene, and 3-methyl-1-butene to an isomerization/metathesis reactor including a first reaction zone comprising an isomerization catalyst and a second reaction zone comprising a first metathesis catalyst; contacting the $C_5$-olefin stream with the isomerization catalyst in the first reaction zone to form an isomerization product comprising internal-pentenes including at least one of 2-pentenes and 2-methyl 2-butene; contacting the internal pentenes with ethylene in the presence of the metathesis catalyst in the second reaction zone to form a first metathesis product comprising propylene and butenes, including at least one of 1-butene and isobutene, as well as any unreacted ethylene and unreacted $C_5$ olefins; feeding the first metathesis product to a fractionation system; fractionating the first metathesis product in the fractionation system to form an ethylene fraction, a propylene fraction, a butene fraction, and a pentene fraction; feeding the propylene fraction to a metathesis reactor and contacting the propylene with a second metathesis catalyst, which may be the same or different than the first metathesis catalyst, to convert at least a portion of the propylene to ethylene and 2-butene and recover a second metathesis product; and feeding the second metathesis product to the fractionation system.

In another aspect, embodiments disclosed herein relate to a system for the production of $C_4$ olefins. The system may include: a flow conduit for feeding ethylene and a $C_5$-olefin stream comprising a mixture of $C_5$ olefins including at least one of 1-pentenes, 2-methyl-1-butene, and 3-methyl-1-butene to an isomerization/metathesis reactor including a first reaction zone comprising an isomerization catalyst and a second reaction zone comprising a first metathesis catalyst; the isomerization/metathesis reactor for contacting the $C_5$-olefin stream with the isomerization catalyst in the first reaction zone to form an isomerization product comprising internal-pentenes including at least one of 2-pentenes and 2-methyl-2-butene, and for contacting the internal pentenes with the metathesis catalyst in the second reaction zone to form a first metathesis product comprising propylene and butenes, including at least one of 1-butene and isobutene, as well as any unreacted ethylene and unreacted $C_5$ olefins; a fractionation system for fractionating the first metathesis product in the fractionation system to form an ethylene fraction, a propylene fraction, a butene fraction, and a pentene fraction; a metathesis reactor for contacting the propylene fraction with a second metathesis catalyst, which may be the same or different than the first metathesis catalyst, to convert at least a portion of the propylene to ethylene and 2-butene and recover a second metathesis product; and a flow conduit for feeding the second metathesis product to the fractionation system.

Other aspects and advantages will be apparent from the following description and the appended claims.

DETAILED DESCRIPTION

Figure 1:
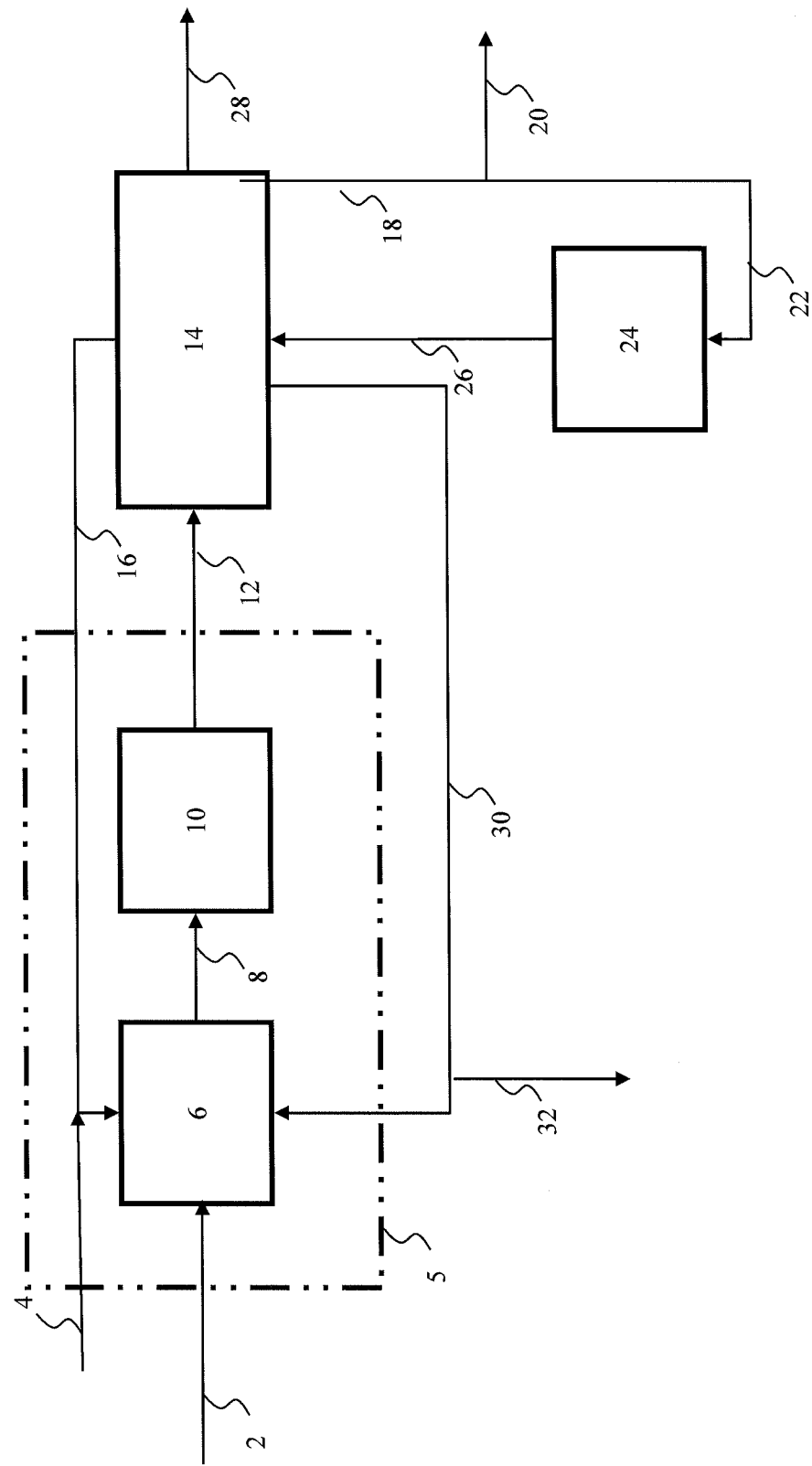
FIG. 1 is a simplified process flow diagram of a process for producing butenes according to embodiments disclosed herein.

In one aspect, embodiments herein relate to the processing of $C_5$ hydrocarbons to form lighter olefins, such as butenes. In another aspect, embodiments disclosed herein relate to the conversion of $C_5$ olefins to butene via an integrated isomerization and metathesis process, and to production of butadienes via cracking of the butene products. Embodiments disclosed herein provide systems and processes for the production of $C_4$ olefins.

Feedstocks useful in embodiments herein include various $C_5$-containing hydrocarbon streams, especially those containing alpha-pentenes, including 1-pentene, 2-methyl 1-butene, and 3-methyl 1-butene. Mixed pentene feedstocks useful in embodiments disclosed herein may include linear pentenes and isopentenes. Mixed pentene feedstocks may also include various other hydrocarbon components, including $C_4$ to $C_6$ paraffins and olefins. In some embodiments, the mixed pentene feedstock may be a $C_5$ hydrocarbon fraction from a catalytic or steam cracker, where the $C_5$ fraction may include linear pentenes, isopentene, n-pentanes, and isopentanes. In some embodiments, the mixed pentene feedstock may include isopentene at a concentration of greater than 40 mol %, 50 mol %, or 60 mol %.

The alpha-pentenes in the hydrocarbon stream may be contacted with an isomerization or hydroisomerization catalyst to form an isomerization product comprising internal-pentenes, such as converting 1-pentenes to 2-pentenes, and 2-methyl 1-butene and 3-methyl 1-butene to 2-methyl 2-butene. Ethylene and the internal-pentenes may then be contacted with a first metathesis catalyst to form a first metathesis product comprising butenes, including 1-butene and isobutene, and propylene, as well as any unreacted ethylene and $C_{5+}$ olefins. The first metathesis product may then be fractionated to form an ethylene fraction, a propylene fraction, a butene fraction, and a $C_{5+}$ fraction.

The propylene fraction, or a portion thereof, may be recovered as a product stream. Alternatively or additionally, production of butenes in the process may be increased via contacting of the propylene with a second metathesis catalyst, which may be the same or different than the first metathesis catalyst, to convert at least a portion of the propylene to ethylene and 2-butene and form a second metathesis product. The first metathesis product and the second metathesis product may be fractionated in a common fractionation system in some embodiments. Providing an additional propylene metathesis stage provides flexibility in the product mixture, allowing one to adjust the rate of withdrawing the propylene product stream to produce a selected ratio of butene to propylene product.

The ethylene fraction and the $C_{5+}$ fraction may also be recycled to the isomerization stage or the pentene metathesis stage to increase the overall conversion of the ethylene and pentenes in the system.

Prior to isomerization and metathesis, some pre-processing of the $C_5$ olefin-containing stream may be desired. For example, it is generally desirable to limit the content of cyclopentene and/or dienes in the hydrocarbon stream fed to isomerization. In some embodiments, the process may include fractionating a $C_5$ olefin-containing hydrocarbon stream to form the $C_5$ feed to the isomerization stage. Depending upon the tolerance of the catalyst to cyclopentene, it may be desirable to limit the amount of cyclopentene in the feed. In some embodiments, the hydrocarbon mixture recovered from the fractionation contains less than 0.5 wt % cyclopentene; less than 0.4 wt %, less than 0.3 wt %, and less than 0.25 wt % in other embodiments. It may also be desired to selectively hydrogenating dienes in the hydrocarbon stream prior to, subsequent to, or concurrent with the above-noted fractionation stage to remove cyclopentenes. For example, catalytic distillation may be used to concurrently selectively hydrogenate dienes and separate cyclopentenes from the C5 feedstock.

Following recovery, the butene fraction may be further processed, if desired, to form butadiene or other end products. For example, butadiene may be produced by dehydrogenation of the butene fraction. Isobutene may also be separated from normal butenes in the butene fraction via at least one of isomerization and fractionation. The isobutene may then undergo skeletal isomerization to form additional normal butenes; alternatively, the isobutene may be etherified to produce MTBE, ETBE or other end products.

Referring now to FIG. 1, a simplified process flow diagram of a process for the production of $C_4$ olefins according to embodiments herein is illustrated. A $C_5$-olefin containing stream 2, which may include one or more $C_5$ olefins such as at least one of 1-pentenes, 2-methyl 1-butene, and 3-methyl 1-butene, may be fed to an isomerization/metathesis reaction system 5. The isomerization/metathesis reaction system 5 may include a first reaction zone 6, including one or more reactors in parallel or series, each containing an isomerization catalyst. The isomerization/metathesis reaction system 5 may also include a second reaction zone 10, including one or more reactors in parallel or series, each containing a metathesis catalyst.

Figure 3:
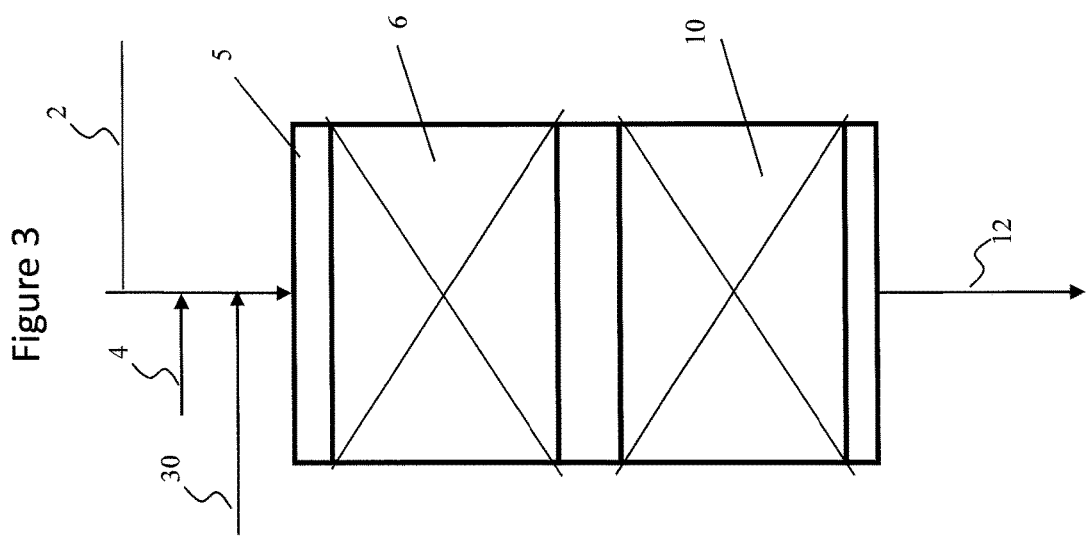
FIG. 3 is a simplified process flow diagram of an isomerization/metathesis reactor for use in processes for producing butenes according to embodiments disclosed herein.

In other embodiments, such as illustrated in FIG. 3, where like numerals represent like parts, the isomerization/metathesis reaction system 5 includes one or more reactors in parallel, each including a first (upstream) isomerization reaction zone 6 and a second (downstream) metathesis reaction zone 10. When contained in the same reactor, it is preferred that the isomerization catalyst beds 6 be segregated from the metathesis reaction beds 10 such that isomerization and metathesis of the desired butene reaction products does not occur, such as would occur where the isomerization and metathesis catalysts are mixed together, as is common in other isomerization and metathesis processes for producing propylene from $C_5$ olefins. In some embodiments, the isomerization/metathesis reactor 5 is a downflow reactor, the isomerization reaction zone 6 including one or more beds of isomerization catalyst in an upper portion of the reactor and the metathesis reaction zone 10 including one or more beds of metathesis catalyst in a lower portion of the reactor.

In the first reaction zone 6, the $C_5$ olefins and the ethylene are contacted with the isomerization catalyst, and reacted at suitable reaction conditions, to form an isomerization product stream 8 including internal-pentenes, such as 2-pentenes and 2-methyl 2-butene. Isomerization reaction conditions may include temperatures in the range from 20° C. to about 600° C., such as about 200° C. to about 400° C., and pressures in the range from about 14 psig to about 2000 psig, such as about 200 psig to about 600 psig. The first reaction zone 6 may be configured and operated such that an equilibrium mixture rich in internal pentenes is achieved. For example, an equilibrium mixture at operating conditions of about 300° C. and 400 psig may have a high ratio of internal olefins relative to alpha olefins, such as a 2-pentene to 1-pentene ratio of about 6 (about 5 to about 7) and a 2-methyle-2-butene to 3-methyl-1-butene plus 2-methyl-1-butene ratio of about 2 (about 1.5 to about 2.5) for feed to the downstream metathesis reaction zone.

The internal pentenes in isomerization product stream 8 may then be contacted with the metathesis catalyst in the second reaction zone 10 at suitable reaction conditions to form a first metathesis product 12. First metathesis product 12 may include propylene and butenes, including at least one of 1-butene and isobutene, as well as any unreacted ethylene and unreacted $C_5$ olefins.

Ethylene stream 4 may be fed to reaction system 5 at any point upstream of metathesis reaction zone 10. For example, ethylene may be co-fed with the $C_5$ olefin stream 2 to isomerization reaction zone 6. When fed to isomerization reaction zone 6, the ethylene is essentially unaffected by the isomerization catalyst. In other embodiments, the ethylene may be fed intermediate reaction zone 6 and reaction zone 10. For reactors including multiple beds of metathesis catalyst, additional ethylene may be fed intermediate the multiple beds, if desired.

The metathesis product 12 may then be fed to a fractionation system 14 for separation and recovery of the various products and any unreacted feed components. In some embodiments, such as illustrated, the metathesis product 12 may be fractionated in the fractionation system 14 to form an ethylene fraction 16, a propylene fraction 18, a butene fraction 28, and a pentene ($C_5$ or $C_{5+}$) fraction 30. Ethylene fraction 16 and/or pentene fraction 30 may be recycled to reaction zone 5. A $C_{5+}$ purge 32 may also be withdrawn to limit the buildup of various heavy or unwanted compounds within the system.

The propylene fraction 18 may be fed to a metathesis reaction zone 24, which may include one or more reactors or reaction zones operating in series or parallel, each containing a metathesis catalyst, which may be the same or different than the metathesis catalyst in reaction zone 10. The propylene may then be contacting with the metathesis catalyst at appropriate reaction conditions to convert at least a portion of the propylene to ethylene and 2-butene. A propylene auto-metathesis product 26 may then be recovered from reactor 24 and fractionated to recover the ethylene, 2-butene, and any unreacted propylene. In some embodiments, metathesis product 26 may be fed to fractionation system 14 for separation along with metathesis product 12 to recover the desired products and recycle streams. As noted above, a propylene product stream 20 may be withdrawn, as desired.

Figure 2:
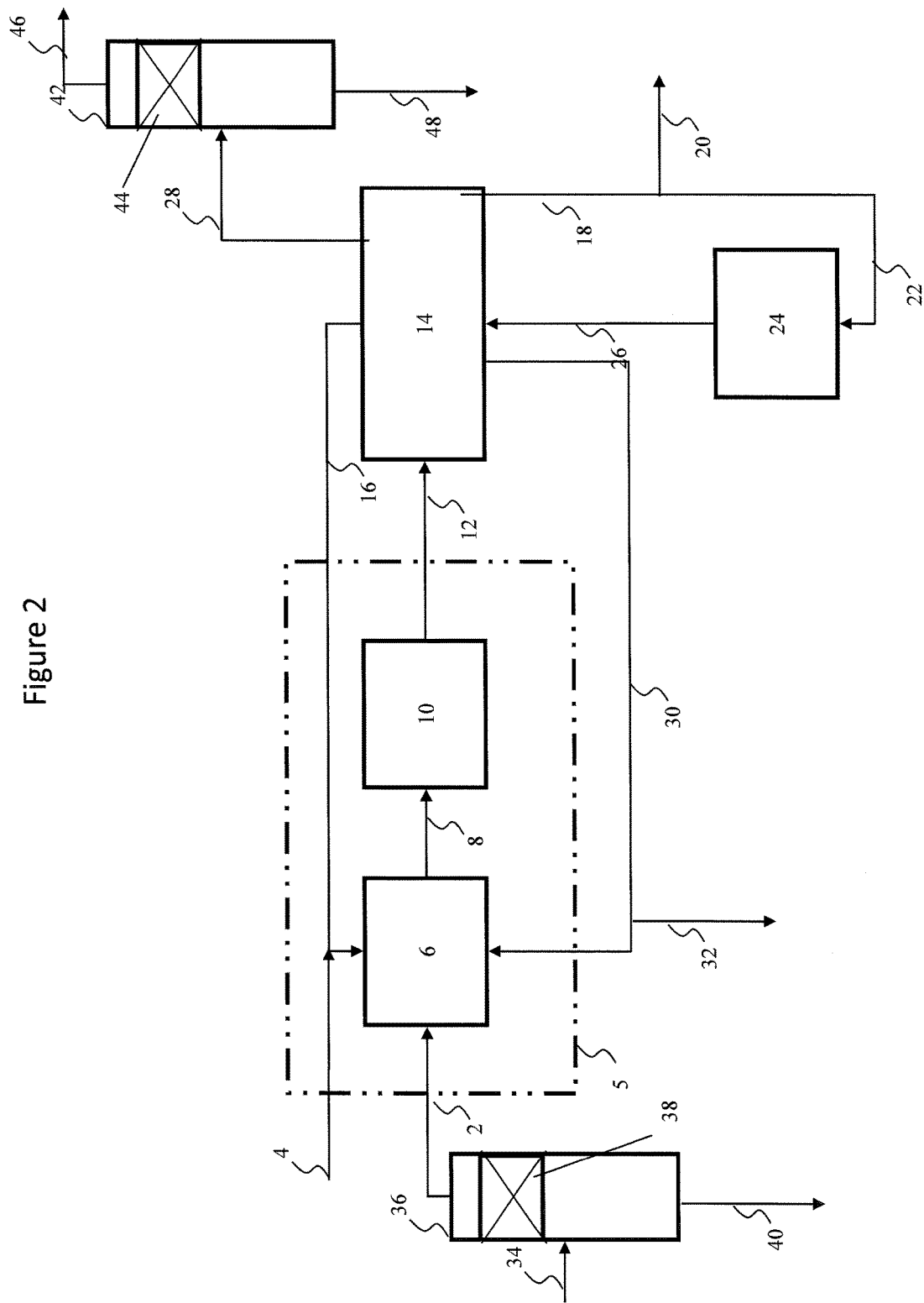
FIG. 2 is a simplified process flow diagram of a process for producing butenes according to embodiments disclosed herein.

Referring now to FIG. 2, a simplified process flow diagram of a process for the production of $C_4$ olefins according to embodiments herein is illustrated, where like numerals represent like parts. In this embodiment, a mixed $C_5$ feed stream 34 is pre-processed to form $C_5$ olefin feed stream 2. As illustrated, the mixed $C_5$ stream 34, which may include dienes (linear, pentadienes; branched, isoprene, and cyclic, cyclopentadiene) may be fed to a catalytic distillation reactor system 36 for concurrent reaction and separation of the dienes and other heavy $C_5$ components in the feed (such as pentanes, if present). The dienes may be converted via hydrogenation into their corresponding olefins in reaction zone 38. Additionally, cyclopentadiene may be converted via dimerization to form dicyclopentadiene, which may be recovered along with the other heavy components in bottoms stream 40. Fractionation and hydrogenation conditions in catalytic distillation reactor system 36 may be selected to limit the diene content in the overheads 2, as well as to limit the amount of cyclopentene in the overheads 2, if necessary.

The process of FIG. 2 also illustrates one possibility for downstream processing of butene product stream 28. As illustrated, butene product stream 28, which includes 1-butene and isobutene, may be fed to a catalytic distillation reactor system 42, which may include one or more reaction zones 44 containing an isomerization catalyst. In catalytic distillation reactor system 42, the 1-butene may be isomerized to form 2-butene to facilitate the concurrent separation of isobutene in the butene fraction 28 from the normal butenes. The separated products, isobutene 46 and 2-butene 48, may then be used separately in downstream processes, as desired.

The above-described $C_5$-to-$C_4$ olefin conversion process (V2IV-OCT™) allows for the production of $C_4$ olefins (isobutene+n-butenes) from any raw industrial streams that contain pentenes (linear, branched, and cyclic). Such streams are readily available from various industrial process streams that contain $C_5$ olefins, such as those found in: crude fractions, MTO (Methanol to Olefins) by-product streams; steam cracker pyrolysis gasoline streams; and FCC (Fluid Catalytic Cracking) recovery streams. Only a small amount of additional ethylene is required for the production of butenes from the $C_5$ olefins.

The first step in some embodiments of the process is to attain a $C_5$ feed essentially free of $C_5$ dienes (such as less than 1000 ppm). This may be achieved via selective hydrogenation of various $C_5$ dienes and fraction. The selective hydrogenation provides for increasing the potential useful $C_5$ olefins such as linear pentenes from linear pentadienes. The raw $C_5$s may also be fractionated and hydrogenated simultaneously via reactive distillation processes. Butenes may then be produced from pentenes via the utilization of isomerization and metathesis. In some embodiments, the metathesis catalysts may be tungsten oxide on silica, and the double-bond isomerization catalyst may be magnesium oxide. The overall process, with propylene metathesis, requires two separate reactors, a S-OCU (segregated olefin conversion unit) reactor and a metathesis-only reactor, and a simple separation train that includes a deethylenizer, a depropylenizer, and a debutenizer.

Processes according to embodiments herein provide for the conversion of both linear and branched $C_5$ olefins into linear butanes and isobutene, respectively. The isobutene in the $C_4$ product stream can be further separated via a isomerization and distillation (concurrently, in a catalytic distillation deisobutenizer (CD-DeIB™), or serially). The isobutene may then be processed further, such as via skeletal isomerization, to generate additional n-butenes if desired.

Processes disclosed herein may allow a producer increased flexibility for managing their olefins portfolio and the ability to adapt to dynamic market conditions. Processes herein provide a completely new method for producing butenes, recently growing in demand, using low-value $C_5$ olefins as feedstock.

As shown in FIG. 2, the overhead process stream 2 from the catalytic distillation reactor 36, is sent to the reaction zone 5. Stream 2, which primarily consists of linear pentenes and branched $C_5$ olefins and is essentially free of $C_5$ dienes with limited amounts of cyclopentene, is used to produce both linear and branched butenes via the overall $C_5$-to-$C_4$ process. These streams may contain some $C_5$ and $C_4$ alkanes that are essentially inert in all subsequent reactors (reactors 1 and 2) but need to be purged from various locations to avoid building up in the process loops.

In the upstream double-bond isomerization section 6, double-bond isomerization of the n-pentenes and branched pentenes are the only reactions (reaction 1, reaction 2, and reaction 3) that occur and provides an equilibrium mixture of pentenes rich in internal double bond pentenes (beta-pentenes, such as 2-pentene and 2-methyl-2-butene) at the starting point of the downstream metathesis catalyst reaction zone 10.

1-pentene←→2-pentene   (Reaction 1)

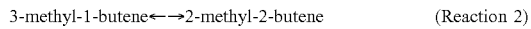
3-methyl-1-butene←→2-methyl-2-butene   (Reaction 2)

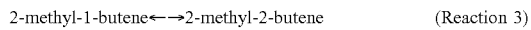
2-methyl-1-butene←→2-methyl-2-butene   (Reaction 3)

In the downstream metathesis section 10, as the cross-metathesis reactions with ethylene are non-productive for any alpha-olefin, such as 1-pentene, 2-methyl-1-butene, and 3-methyl-1-butene, only the following net reactions occur in the metathesis section 10 that produce propylene and butenes (isobutene and 1-butene).

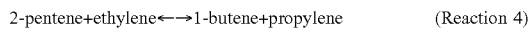
2-pentene+ethylene←→1-butene+propylene   (Reaction 4)

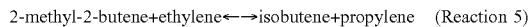
2-methyl-2-butene+ethylene←→isobutene+propylene   (Reaction 5)

The metathesis reactor effluent is then fed to the primary separation train, which may include a deethylenizer, depropylenizer, and debutenizer. The product butenes are separated from the debutenizer overhead stream and may be sent to a CD-DeiB that allows for the product to be separated into isobutene and linear n-butenes. The linear n-butenes stream can be used for producing butadiene or other products. The isobutene stream can be sent to a MTBE unit for production of MTBE or sent to a skeletal isomerization unit for conversion into additional linear butenes if desired.

The separated propylene from the depropylenizer overhead stream may be sent to a metathesis-only reactor (reactor 24) to form additional 2-butene products and ethylene recycle. This reaction can be written as:

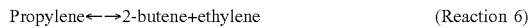
Propylene←→2-butene+ethylene   (Reaction 6)

The product stream containing 2-butene, ethylene and unreacted propylene is added back to the beginning of the separation train for separation and recycle of ethylene and propylene. Ethylene formed from reaction 6 is separated via the deethylenizer and recycled back to the reaction zone 5, thus lowering the requirements for fresh ethylene feed 4, which may be limited for some producers.

Depending on the cyclopentene in the overhead stream 2 from unit 36 entering the reaction zone 5, purge 32 may be taken from the $C_5$ recycle stream 30 to prevent cyclopentene and other $C_{5+}$ heavies buildup in the loop.

The depropylenizer overhead stream can be split to produce polymer-grade propylene, for cases where the client may need some propylene on-demand, and feed to the metathesis only reactor zone 24 to produce butenes. The relative production rates for butenes and propylene product can be essentially controlled by how much is withdrawn via stream 20. Therefore, the V2IV-OCT process provides additional flexibility for managing olefins production between propylene and butenes, using pentenes as feed stock.

Embodiments disclosed herein also relate to a system for the production of $C_4$ olefins. The system may include a flow conduit for feeding ethylene and a $C_5$ olefin stream comprising a mixture of $C_5$ olefins including at least one of 1-pentenes, 2-methyl-1-butene, and 3-methyl-1-butene to an isomerization/metathesis reactor including a first reaction zone comprising an isomerization catalyst and a second reaction zone comprising a first metathesis catalyst. The system also includes the isomerization/metathesis reactor for contacting the $C_5$ olefin stream with the isomerization catalyst in the first reaction zone to form an isomerization product comprising internal-pentenes including at least one of 2-pentenes and 2-methyl 2-butene, and for contacting the internal pentenes with the metathesis catalyst in the second reaction zone to form a first metathesis product comprising propylene and butenes, including at least one of 1-butene and isobutene, as well as any unreacted ethylene and unreacted $C_5$ olefins. A fractionation system may then be used for fractionating the first metathesis product in the fractionation system to form an ethylene fraction, a propylene fraction, a butene fraction, and a pentene fraction.

In some embodiments, the system may also include a metathesis reactor for contacting the propylene fraction with a second metathesis catalyst, which may be the same or different than the first metathesis catalyst, to convert at least a portion of the propylene to ethylene and 1-butene and recover a second metathesis product. A flow conduit may also be provided for feeding the second metathesis product to the fractionation system.

In embodiments disclosed herein, the isomerization/metathesis reactor 5, 6, 10, and/or the metathesis reactor 24 may be operated at a pressure between 2 and 40 atmospheres, and between 5 and 15 atmospheres in other embodiments. The reactors may be operated such that the reaction temperature is within the range from about 30° C. to about 600° C.; within the range from about 200° C. to about 450° C. in other embodiments; and from about 250° C. to about 400° C. in yet other embodiments. The isomerization and metathesis reactions may be performed at a weight hourly space velocity (WHSV) in the range from about 2 to about 200 in some embodiments, and from about 6 to about 40 in other embodiments.

The reactions may be carried out by contacting the olefin(s) with the isomerization and/or metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reactions may be conducted in the absence of significant amounts of deactivating materials such as water and oxygen.

The contact time needed to obtain a desirable yield of reaction products depends upon several factors such as the activity of the catalyst, temperature, pressure, and the structure of the olefin(s) to be isomerized and/or metathesized. Length of time during which the olefin(s) are contacted with catalyst can vary between 0.1 seconds and 4 hours, preferably from about 0.5 sec to about 0.5 hrs. The isomerization and metathesis reactions may be conducted batch-wise or continuously with fixed catalyst beds, slurried catalyst, fluidized beds, or by using any other conventional contacting techniques.

The catalyst contained within the metathesis reactor may be any known metathesis catalyst, including oxides of Group VIA and Group VIIA metals on supports. Catalyst supports can be of any type and could include alumina, silica, mixtures thereof, zirconia, magnesia, titania, and zeolites. In some embodiments, the metathesis catalyst is tungsten oxide on silica.

The double bond isomerization catalyst may be any known double bond isomerization catalyst. In some embodiments, the double bond isomerization catalyst may be one of magnesium oxide, calcium oxide, aluminum oxide, or mixed Mg—Al oxides (e.g, hydrotalcite-derived mixed oxides), among other possible catalysts.

In some embodiments, the double bond isomerization catalyst may be an alumina-titania catalyst. The catalyst may be a γ-alumina-titania crystalline mixture including active sites that catalyze the positional isomerization of olefins, and may be in the form of pellets, extrudates, and the like, and will typically have an effective diameter of 0.5 mm to 5 mm, such as in the range from 1 mm to 4 mm, or in the range from 2 mm to 3 mm. In some embodiments, the alumina-titania catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. γ-Alumina-titania catalyst herein may have a surface area in some embodiments greater than 200 $m^2/g$, in other embodiments greater than 250 $m^2/g$, in other embodiments greater than 300 $m^2/g$, in other embodiments greater than 350 $m^2/g$, and in other embodiments greater than 400 $m^2/g$. The γ-alumina-titania catalysts may be tolerant of oxygenated species that are typically considered a poison, such as to MgO type catalysts, may act as an oxygenate scavenger protecting downstream catalyst beds, and in some embodiments may have activity for dehydration of alcohols in addition to isomerization activity. The γ-alumina-titania catalysts may also be more forgiving with respect to cyclopentene purity of the feed, and may allow greater than 5 wt %, greater than 7.5 wt %, or even greater than 10 wt % cyclopentene to be present in the feed, potentially negating typical upstream processes required to remove cyclopentene from the feed. These γ-alumina-titania catalysts may be used alone, such as in an isomerization only reactor or in an isomerization catalyst bed in a segregated OCU, or may be used in admixture with other isomerization catalysts or metathesis catalysts.

The effluent from the metathesis reactor may be sent to a separation system to separate the metathesis effluent into carbon number groups by technology well known in the art. For example, the products of the separation system may include an ethylene stream, a propylene stream, a $C_4$ stream, and a $C_{5+}$ stream. The propylene stream may be recovered as a product stream, which may also undergo further purification steps to obtain a high purity propylene product. The $C_5$ stream may be recycled back to the metathesis reactor or a pre-treatment stage, such as isomerization or fractionation. The ethylene stream may be recovered as a product stream or may be recycled back to the metathesis reactor for use as an ethylene feedstock for the conventional metathesis reaction.

As described above, embodiments disclosed herein provide an efficient process for converting mixed pentenes to butenes. Advantageously, embodiments herein may provide for conversion of a low-value feedstock, $C_5$s, to a higher valued end product, including butenes and optionally propylene. The conversion may be accomplished with little or no overall net consumption of ethylene. Processes disclosed herein also provide additional flexibility for managing olefins production between propylene and butenes using pentenes as a feedstock.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system for the production of $C_4$ olefins, the system comprising:
    an isomerization reaction zone for contacting a hydrocarbon mixture comprising alpha-pentenes with an isomerization catalyst to form an isomerization product comprising beta-pentenes;
    a first metathesis reaction zone for contacting ethylene and the beta-pentenes with a first metathesis catalyst to form a first metathesis product comprising butenes and propylene, as well as any unreacted ethylene and $C_5$ olefins;
    a separation system for fractionating the first metathesis product to form an ethylene fraction, a propylene fraction, a butene fraction, and a $C_5$ fraction; and
    a second metathesis reaction zone for contacting the propylene with a second metathesis catalyst, which may be the same or different than the first metathesis catalyst, to convert at least a portion of the propylene to ethylene and 2-butene and form a second metathesis product.

2. The system of claim 1, further comprising a flow conduit for feeding the first metathesis product and the second metathesis product to a common fractionation system.

3. The system of claim 2, further comprising a flow conduit for withdrawing a propylene product stream.

4. The system of claim 3, further comprising a control system for adjusting a rate of withdrawing the propylene product stream to produce a selected ratio of butene to propylene product.

5. The system of claim 1, further comprising one or more flow conduits for recycling at least one of the ethylene fraction or the $C_5$ fraction to at least one of the isomerization reaction zone or the first metathesis reaction zone.

6. The system of claim 1, further comprising at least one of:
    a separation zone or a reaction/separation zone for separating isobutene in the butene fraction from normal butenes in the butene fraction via at least one of isomerization and fractionation;
    a reaction zone comprising a catalyst for the skeletal isomerization of the isobutene to form normal butenes; or
    a reaction zone for etherifying the isobutene.

7. A system for the production of $C_4$ olefins, the process comprising:

one or more flow conduits for feeding, together or separately, ethylene and a $C_5$ olefin stream comprising a mixture of $C_5$ olefins including at least one of 1-pentenes, 2-methyl-1-butene, or 3-methyl-1-butene to an isomerization/metathesis reactor including a first reaction zone comprising an isomerization catalyst and a second reaction zone comprising a first metathesis catalyst;

the isomerization/metathesis reactor for contacting the $C_5$-olefin stream with the isomerization catalyst in the first reaction zone to form an isomerization product comprising internal-pentenes including at least one of 2-pentenes or 2-methyl 2-butene and for contacting the internal pentenes with ethylene in the presence of the metathesis catalyst in the second reaction zone to form a first metathesis product comprising propylene and butenes, including at least one of 1-butene or isobutene, as well as any unreacted ethylene and unreacted $C_5$ olefins;

a fractionation system for fractionating the first metathesis product in the fractionation system to form an ethylene fraction, a propylene fraction, a butene fraction, and a pentene fraction;

a metathesis reactor for contacting the propylene with a second metathesis catalyst, which may be the same or different than the first metathesis catalyst, to convert at least a portion of the propylene to ethylene and 2-butene and recover a second metathesis product;

a flow conduit for feeding the second metathesis product to the fractionation system.

8. The system of claim 7, wherein the flow conduit for feeding the ethylene to the isomerization/metathesis is disposed for feeding the ethylene to the reactor intermediate the first reaction zone and the second reaction zone.

9. The system of claim 7, further comprising one or more flow conduits for recycling at least one of the ethylene fraction or the pentene fraction to the isomerization/metathesis reactor.

10. The system of claim 7, further comprising a separation zone for fractionating a hydrocarbon stream comprising mixed $C_5$ hydrocarbons to form the C5 olefin stream, wherein the C5 olefin stream comprises less than 0.5 wt % cyclopentene.

11. The system of claim 10, further comprising a reaction zone for selectively hydrogenating dienes in at least one of the hydrocarbon stream or the C5 olefin stream.

12. The system of claim 7, further comprising at least one of:
a separation system for separating isobutene in the butene fraction from normal butenes in the butene fraction via at least one of isomerization and fractionation;
a reaction zone for skeletal isomerizing the isobutene to form normal butenes;
a reaction zone for etherifying the isobutene.

13. The system of claim 7, further comprising a flow conduit for withdrawing a propylene product stream.

14. The system of claim 13, further comprising a control system for adjusting a rate of withdrawing the propylene product stream to produce a selected ratio of butene to propylene product.

15. The system of claim 7, wherein the isomerization/metathesis reactor is a downflow reactor, the isomerization reaction zone comprising one or more beds of isomerization catalyst in an upper portion of the reactor and one or more beds of metathesis catalyst in a lower portion of the reactor.

16. A system for the production of $C_4$ olefins, the system comprising:
an isomerization/metathesis reactor including
a first reaction zone comprising an isomerization catalyst;
a second reaction zone comprising a first metathesis catalyst;
an inlet for introducing a $C_5$-olefin stream comprising a mixture of $C_5$ olefins including at least one of 1-pentenes, 2-methyl-1-butene, and 3-methyl-1-butene to the isomerization/metathesis reactor for contacting the $C_5$-olefin stream with the isomerization catalyst in the first reaction zone to form an isomerization product comprising internal-pentenes including at least one of 2-pentenes or 2-methyl-2-butene;
an inlet for introducing ethylene to the isomerization/metathesis reactor for contacting the ethylene and the internal pentenes with the metathesis catalyst in the second reaction zone to form a first metathesis product comprising propylene and butenes, including at least one of 1-butene or isobutene, as well as any unreacted ethylene and unreacted $C_5$ olefins;
a metathesis reactor for contacting a propylene fraction with a second metathesis catalyst, which may be the same or different than the first metathesis catalyst, to convert at least a portion of the propylene to ethylene and 2-butene and recover a second metathesis product;
a fractionation system for fractionating the first metathesis product and the second metathesis product to form an ethylene fraction, the propylene fraction, a butene fraction, and a pentene fraction.

17. The system of claim 16, further comprising a control system and associated flow conduits to selectively withdraw a propylene product stream and control a ratio of butene product to propylene product.

18. The system of claim 16, further comprising a recycle stream for recycling a portion of the pentene fraction to the isomerization/metathesis reactor, and a purge stream for purging a portion of the pentene fraction.

19. The system of claim 16, further comprising a catalytic distillation reactor system for concurrent reaction and separation of a mixed C5 hydrocarbon-containing stream, wherein the catalytic distillation reaction system comprises a selective hydrogenation reaction zone, the catalytic distillation reactor system further configured to recover the $C_5$-olefin stream comprising a mixture of $C_5$ olefins.

20. The system of claim 16, further comprising a catalytic distillation reactor system for concurrent reaction and separation of the butene fraction, wherein the catalytic distillation reactor system comprises an isomerization reaction zone.

* * * * *